United States Patent
Voskoboynikov et al.

(10) Patent No.: US 10,668,455 B2
(45) Date of Patent: Jun. 2, 2020

(54) HETEROGENIZED CATALYST FOR ACETYLENE DIMERIZATION

(71) Applicant: UOP LLC, Des Plaines, IL (US)

(72) Inventors: Timur V. Voskoboynikov, Arlington Heights, IL (US); Alakananda Bhattacharyya, Glen Ellyn, IL (US); Nikolay Y. Adonin, Novosibirsk (RU); Mariya N. Timofeeva, Novosibirsk (RU); Sergey A. Prikhodko, Novosibirsk (RU); Valentin N. Parmon, Novosibirsk (RU)

(*) Notice: Subject to any disclaimer, the term of this patent is extended or adjusted under 35 U.S.C. 154(b) by 0 days.

(21) Appl. No.: 16/221,316

(22) Filed: Dec. 14, 2018

(65) Prior Publication Data

US 2019/0118169 A1  Apr. 25, 2019

Related U.S. Application Data

(63) Continuation of application No. PCT/US2016/038796, filed on Jun. 22, 2016.

(51) Int. Cl.

| | | |
|---|---|---|
| *B01J 31/08* | (2006.01) | |
| *C07C 2/38* | (2006.01) | |
| *B01J 23/72* | (2006.01) | |
| *B01J 27/13* | (2006.01) | |
| *B01J 27/236* | (2006.01) | |
| *B01J 27/128* | (2006.01) | |
| *B01J 47/016* | (2017.01) | |
| *B01J 41/13* | (2017.01) | |
| *B01J 31/30* | (2006.01) | |

(Continued)

(52) U.S. Cl.
CPC ............ *B01J 31/08* (2013.01); *B01J 23/72* (2013.01); *B01J 27/128* (2013.01); *B01J 27/13* (2013.01); *B01J 27/236* (2013.01); *B01J 31/30* (2013.01); *B01J 41/10* (2013.01); *B01J 41/13* (2017.01); *B01J 41/14* (2013.01); *B01J 41/16* (2013.01); *B01J 47/016* (2017.01); *C07C 2/38* (2013.01); *C07C 5/09* (2013.01); *B01J 2231/20* (2013.01); *C07C 11/167* (2013.01); *C07C 11/28* (2013.01); *C07C 2531/08* (2013.01)

(58) Field of Classification Search
CPC . B01J 31/08; B01J 47/016; B01J 41/13; B01J 31/30; B01J 41/10; B01J 41/14; B01J 41/16; C07C 2/38; C07C 5/09; C07C 11/167; C07C 11/28; C07C 2531/08
USPC .... 502/159, 162, 169; 585/1, 252, 255, 317, 585/505, 601
See application file for complete search history.

(56) References Cited

U.S. PATENT DOCUMENTS

| | | | | |
|---|---|---|---|---|
| 2,861,045 A | * | 11/1958 | Langer, Jr. ............... | B01J 31/10 502/159 |
| 3,406,215 A | * | 10/1968 | Holmquist ............... | C07C 17/10 570/235 |

(Continued)

OTHER PUBLICATIONS

Written Opinion for PCT/US2016/038796. (dated Year: 2017).*

*Primary Examiner* — Patricia L. Hailey (57) ABSTRACT

A catalyst and a process for using the catalyst are presented. The catalyst is a heterogeneous catalyst and includes active metal halides bonded to functional groups. The functional groups are bonded to a polymeric backbone to form the structure supporting the catalyst. The catalyst is useful for the dimerization of acetylene to convert the acetylene to a larger hydrocarbon, and in particular to dimerize acetylene to vinylacetylene.

4 Claims, 5 Drawing Sheets

(51) Int. Cl.
  *B01J 41/10*  (2006.01)
  *B01J 41/14*  (2006.01)
  *B01J 41/16*  (2006.01)
  *C07C 5/09*   (2006.01)
  *C07C 11/167* (2006.01)
  *C07C 11/28*  (2006.01)

(56) References Cited

U.S. PATENT DOCUMENTS

| | | | |
|---|---|---|---|
| 3,578,626 A * | 5/1971 | Kornicker | C08F 10/00 528/392 |
| 3,800,000 A * | 3/1974 | Fahey | B01J 31/143 585/301 |
| 4,111,856 A * | 9/1978 | Haag | B01J 31/08 502/159 |
| 4,323,698 A * | 4/1982 | Haag | B01J 31/08 502/159 |
| 2014/0058146 A1* | 2/2014 | Bricker | B01J 19/10 585/252 |
| 2016/0049663 A1* | 2/2016 | Sugitani | H01M 8/1004 429/482 |

* cited by examiner

HETEROGENIZED CATALYST FOR ACETYLENE DIMERIZATION

CROSS-REFERENCE TO RELATED APPLICATION

This application is a Continuation of copending International Application No. PCT/US2016/038796 filed Jun. 22, 2016, the contents of which cited application is hereby incorporated by reference in its entirety.

FIELD OF THE INVENTION

The field of the invention relates to the dimerization of acetylene. In particular, the invention relates to a heterogeneous catalyst that can be used in the dimerization of acetylene.

BACKGROUND

The dimerization of acetylene can be accomplished with a Nieuwland catalytic system. A Nieuwland catalyst is composed of copper chloride (CuCl) and potassium chloride (KCl) or ammonium chloride ($NH_4Cl$) in an aqueous media. The process generates monovinylacetylene, with a small amount of divinylacetylene, and without the formation of benzene, or the formation of a linear acetylene trimer, or oligomers.

The use of $CuCl_2$ for the dimerization of acetylene is shown in U.S. Pat. No. 3,957,899. One of the problems with the use of $CuCl_2$ is the low solubility of Cu(I) in a homogeneous solution. The Nieuwland catalyst addresses this by the addition of potassium chloride or ammonium chloride to increase the Cu(I) in solution.

Currently there is no heterogeneous catalyst for the dimerization of acetylene. A good heterogeneous catalyst can improve the conversion of acetylene to higher value products such as vinylacetylene and the process for product separation.

SUMMARY

A catalyst is presented for use in the dimerization of acetylene. A first embodiment comprises an ion exchange resin with an exchangeable anion (hydroxide or halide ion) to form an exchanged resin including the halide; and the exchanged resin is compounded with a metal halide. An embodiment of the catalyst of the prior embodiment includes a halide compound selected from the group consisting of amines, phosphines, and mixtures thereof. An embodiment of the catalyst of the prior embodiment includes an amine that has the form of NR1R2R3, or a phosphine that has the form PR1R2R3. An embodiment of the catalyst of the prior embodiment wherein the R1, R2, R3 groups are selected from the group consisting of hydrogen, alkyl groups, aryl groups, and mixtures thereof. An embodiment of the catalyst of the prior embodiment wherein the R1, R2, R3 groups are the same alkyl group. An embodiment of the invention is one, any or all of prior embodiments in this paragraph up through the first embodiment wherein the metal halide is selected from the group consisting of cuprous chloride (CuCl), silver chloride (AgCl), ferrous chloride ($FeCl_2$), ferric chloride ($FeCl_3$), nickel chloride ($NiCl_2$), chlorides of gold (AuCl and $AuCl_3$), or mixtures thereof. An embodiment of the catalyst of the prior embodiment wherein the metal halide is cuprous chloride. An embodiment of the invention is one, any or all of prior embodiments in this paragraph up through the first embodiment wherein the ion exchange resin comprises a polymer backbone selected from the group consisting of styrene, divinylbenzene, styrene-divinylbenzene co-polymer, polyethylene, polyamine-epichlorohyrdin-$NH_3$ condensate, melamine-formaldehyde condensate, polyamine-phenol-formaldehyde condensate, melamine-formaldehyde condensate, polyamine-phenol-formaldehyde condensate, cellulose and mixtures thereof.

Another embodiment comprises a catalyst comprising a polymer backbone with a plurality of functional groups, wherein the functional groups are selected phosphonium chlorides and amine chlorides; and the functional groups are ion exchanged with metal chlorides. An embodiment of the catalyst of the prior embodiment wherein the polymer backbone is selected from the group consisting of styrene, divinylbenzene, styrene-divinylbenzene co-polymer, polyethylene, polyamine-epichlorohyrdin-$NH_3$ condensate, melamine-formaldehyde condensate, polyamine-phenol-formaldehyde condensate, melamine-formaldehyde condensate, polyamine-phenol-formaldehyde condensate, cellulose and mixtures thereof. An embodiment of the invention is one, any or all of prior embodiments in this paragraph up through the first embodiment in this paragraph wherein the amine in the amine chloride has the form of NR1R2R3, and the phosphine in the phosphonium chloride has the form PR1R2R3. An embodiment of the invention is one, any or all of prior embodiments in this paragraph up through the first embodiment in this paragraph wherein the R1, R2, R3 groups are selected from the group consisting of hydrogen, alkyl groups having from 1 to 4 carbon atoms, aryl groups and mixtures thereof. An embodiment of the invention is one, any or all of prior embodiments in this paragraph up through the first embodiment in this paragraph wherein R1, R2, R3 are selected from the group consisting of H, $CH_3$, $C_2H_5$, or mixtures thereof. An embodiment of the invention is one, any or all of prior embodiments in this paragraph up through the first embodiment in this paragraph wherein the metal chloride is selected from the group consisting of cuprous chloride (CuCl), silver chloride (AgCl), ferrous chloride ($FeCl_2$), ferric chloride ($FeCl_3$), nickel chloride ($NiCl_2$), chlorides of gold (AuCl and $AuCl_3$), or mixtures thereof. An embodiment of the invention is one, any or all of prior embodiments in this paragraph up through the first embodiment in this paragraph wherein the metal chloride is cuprous chloride. An embodiment of the invention is one, any or all of prior embodiments in this paragraph up through the first embodiment in this paragraph wherein the polymer backbone is selected from the group consisting of styrene.

In another embodiment, the invention is a process for the production of 1,3 butadiene, comprising dimerizing a first process stream comprising acetylene in the presence of a catalyst comprising a polymer backbone with a plurality of functional groups affixed to the polymer backbone wherein the functional groups have a positive charge, and at least one of the functional groups is ion exchanged with a metal halide to generate a polymer with metal halide groups ionically bonded to the functional groups, to generate a second process stream comprising vinylacetylene, wherein the functional groups are selected from the group consisting of amines, phosphines and mixtures thereof selectively hydrogenating the vinylacetylene in the second process stream to generate a third process stream comprising 1,3 butadiene. An embodiment of the invention is one, any or all of prior embodiments in this paragraph up through the first embodiment in this paragraph wherein the metal is selected from the group consisting of copper, iron, silver and mixtures thereof. An embodiment of the invention is one, any or all of prior embodiments in this paragraph up through the first embodiment in this paragraph wherein the hydrogenating of vinyl acetylene is performed in a reactor with a selective hydrogenation catalyst. An embodiment of the invention is one, any or all of prior embodiments in this paragraph up through the first embodiment in this paragraph wherein the polymer backbone is selected from the group consisting of styrene, divinylbenzene, styrene-divinylbenzene co-polymer, polyethylene, polyamine-epichlorohyrdin-$NH_3$ condensate, melamine-formaldehyde condensate, polyamine-phenol-formaldehyde condensate, melamine-formaldehyde condensate, polyamine-phenol-formaldehyde condensate, and mixtures thereof.

In the foregoing, all temperatures are set forth in degrees Celsius and, all parts and percentages are by weight, unless otherwise indicated.

Other objects, advantages and applications of the present invention will become apparent to those skilled in the art from the following detailed description and drawings.

DETAILED DESCRIPTION 1,3 Butadiene is an important precursor for the production of butyl rubbers. The primary source of butadiene is derived from the cracking of naphtha or other hydrocarbon feedstocks. However, due to the increased demand for light olefins, ethylene and propylene, the supply of butenes and other C4 hydrocarbons from the cracking process is significantly reduced. With an increase in demand for butyl rubbers, alternate sources of 1,3 butadiene are needed. One such source is the development of on-purpose butadiene technologies.

One source of butadiene production can be generated by the dimerization of acetylene. Technologies are being developed to generate acetylene from natural gas, principally methane, and this provides a source to help meet the demand for butadiene production. The Nieuwland catalyst, a mixture of CuCl and KCl or $NH_4C_1$ catalyzes acetylene to make chemicals that can be converted to butadiene. However, the CuCl catalyst has poor solubility in water, and either an alkali chloride or ammonium chloride needs to be added in a relatively high concentration to generate an aqueous solution where the Cu(I) exists as $CuCl_2^-$ anions.

There has been no serious attempt to make a heterogeneous analog to the Nieuwland catalyst. It is desirable to develop an effective heterogeneous catalyst for acetylene dimerization to overcome some of the drawbacks associated with the Nieuwland catalyst. By using anionites, it is possible to exchange the original $Cl^-$ to $CuCl_2^-$. The support cannot be a traditional support, such as silica, alumina, layered double hydroxides, or generally a refractory oxide or mixture thereof, as they do not generate active catalysts. By varying the nature of anionite, Cu loading and catalyst activation technique (i.e. swelling in organic solvent) it was possible to obtain good performing catalysts.

The present invention is a new catalyst for use in the dimerization of acetylene. The catalyst comprises an ion exchange resin having an exchangeable halide ion to form an exchanged resin. The exchanged resin is then compounded with a metal halide. The resin is exchanged with functional groups, or can be manufactured with the functional groups, to create a polymeric backbone with functional groups attached wherein the functional groups bond with the metal halide. In one embodiment, the functional groups comprise amines, phosphines, and a mixture of amine and phosphine groups on the polymeric backbone.

The polymer backbone for the ion exchange resin can be selected from a variety of polymers and co-polymers, as well as polymer mixtures. Polymers that are useful for the present invention include polymers made from styrene, divinylbenzene, styrene-divinylbenzene co-polymer, polyethylene, polyamine-epichlorohyrdin-$NH_3$ condensate, melamine-formaldehyde condensate, polyamine-phenol-formaldehyde condensate, melamine-formaldehyde condensate, polyamine-phenol-formaldehyde condensate, cellulose and mixtures thereof. In one embodiment, the polymer backbone comprises cross-linked polystyrene.

The amine groups attached to the polymer have the form NR1R2R3, and the phosphine groups have the form PR1R2R3, wherein N is the nitrogen, P is phosphorus, and R1, R2 and R3 are groups selected from hydrogen (H), alkyl groups and aryl groups. In one embodiment, the groups R1, R2, R3 are the same group, either hydrogen, or an alkyl or aryl group. In another embodiment, the groups R1, R2, R3 are selected from alkyl groups having from 1 to 4 carbon atoms.

After the formation of the polymer backbone with the functional groups, either amines or phosphines or both, the resin is exchanged with a metal halide to generate the functional groups complexed with the metal halide ions. The metal for the metal halide are selected form copper (Cu), silver (Ag), iron (Fe), nickel (Ni), gold (Au) and mixtures thereof. The halides in the metal halide include fluorine (F), chlorine (Cl) bromine (Br), iodine (I) and mixtures thereof. In one embodiment, the metal halides are selected from one or more of the following metal halides: cuprous chloride (CuCl), silver chloride (AgCl), ferrous chloride ($FeCl_2$), ferric chloride ($FeCl_3$), nickel chloride ($NiCl_2$), and chlorides of gold (AuCl and $AuCl_3$). A preferred metal halide is cuprous chloride.

One embodiment of the present invention is the use of the catalyst in the production of butadienes. The process includes dimerizing a first process stream comprising acetylene by reacting the acetylene in the presence of a catalyst, wherein the catalyst comprises a polymer backbone with functional groups. The functional groups are ion exchanged with a metal halide to generate the catalyst comprising the polymer backbone with metal halide groups. The dimerization of acetylene generates a second process stream comprising vinylacetylene.

The second process stream is passed to a hydrogenation reactor to generate a third process stream comprising butadienes. The hydrogenation reactor comprises a selective hydrogenation catalyst for hydrogenating the acetylene triple bond.

The catalyst for acetylene dimerization, or oligomerization, is generated by, first allowing the anionite to swell in water. Second, the anionite is treated with an NaOH solution, to convert the functional groups to $OH^-$. Third, the anionite is treated with an HCl solution, to convert the functional groups to Cl⁻. Then, an aqueous solution comprising copper chloride and sodium chloride was prepared. The solution was transferred and allowed to infiltrate through the anionite. The anionite with Cu was washed to remove excess copper, and then the catalyst was dried.

As shown in the diagram, the polymer has amine functional groups on the polymer, and the polymer is bathed with an aqueous solution containing the copper chloride. The copper(I) chloride which exists in solution as $CuCl_2$ anions, is exchanged with Cl⁻ of the polymer, and the copper chloride is immobilized on the polymer at the amine functional groups. Analogs using phosphine functional groups can also be used to generate the catalyst.

In another method of preparation, the copper chloride was immobilized in layer double hydroxides (LDH). The layer double hydroxides were prepared by coprecipitation and sol-gel routes, which are known in the art. The general formula for the layer double hydroxides is:

The layer double hydroxide is stayed under distilled water. The LDH is then mixed with a NaCl solution, and then washed with distilled water. The prepared LDH is then mixed with a solution of CuCl and NaCl to impregnate the CuCl into the LDH.

In preparation for use of the catalyst, the catalyst was mixed with a solvent and allowed to swell. The swelling occurs when molecules penetrate the polymer matrix. The swelling changes the accessibility to the functional groups in the metal-containing anionites. The swelling process is not just the penetration of the solvent into the polymer matrix, but also changes the structure of the polymer, such as by unwinding the polymer chains. The degree of swelling is related to the porosity and donor-acceptor properties of the functional groups of the anionites with respect to the solvent. Solvents tested include water, benzene, ethanol, acetone, N,N-Dimethylformamide, and N-methyl-2-pyrrolidone (NMP).

The catalyst were analyzed using gas chromatography (GC), inductively coupled plasma-atomic emission spectrometry (ICP-AES), X-ray photoelectron spectrometry (XPS), extended X-ray adsorption fine structure (EXAFS) spectrometry, and X-ray adsorption near edge structure (XANES) spectrometry to characterize and understand the structure of the catalysts.

Thirteen polystyrene based anionites were prepared and tested in batch mode under conditions, described below. Under air-free conditions, 50 ml reaction vessel was loaded with 1.3 g of catalyst. For swelling study, an outgassed solvent was added, held, and then excess solvent was purged by Ar flow. Acetylene from a cylinder was purified, dried over solid NaOH, and directed into reaction vessel, kept at desired temperature, under 1000 rpm stirring. Samples for GC analysis were taken from the gas phase by air-tight gas syringe. The best catalysts were also tested under continuous flowing conditions: 2.6 g of catalyst, 15 ml/min acetylene flow, at 65° C.

In addition to the studying of various anionites, the affect of the swelling on activity and stability was studied. The catalysts exhibited good activity and selectivity, with conversions of greater than 7% and with a vinylacetylene selectivity of greater than 85%. During the testing, with on-stream flow of the reactants through the reactor, the molar ratio of converted acetylene to copper exceeded 9, demonstrating the catalytic nature of the reaction and the active copper (Cu) species. The specific activity reached a level of 0.15 mmol/($g_{Cu}$·min). This shows the catalytic activity exceeds that of the conventional Nieuwland homogeneous catalyst by a substantial amount. The conventional Nieuwland catalyst specific activity is 0.03 mmol/($g_{Cu}$·min) in water, and 0.005 mmol/($g_{Cu}$·min) in NMP.

Catalysts that were the best in the dimerization reaction of acetylene are based on cross-linked polystyrene of gel type. In the presence of these catalysts, the selectivity to vinyl acetylene was 87% to 94%. Cross-linked polystyrene serve as a basis of the ion-exchange resins. The cross-linking is achieved through copolymerization of styrene with a small amount of divinyl benzene. Cross-linking improves mechanical properties, and suppresses the undesired solubility of non-cross-linked polystyrene in solvents.

For anion exchangers, there are two types of resins: strongly basic and weakly basic. In a preferred embodiment, the preferred resin is a strongly basic form. The weakly basic anion exchangers have moving protons that can produce a protonated form of the metal halide and which can result in a decrease in the catalyst selectivity, whereas the strongly basic anion exchanger does not have this loss of selectivity.

Figure 1A:
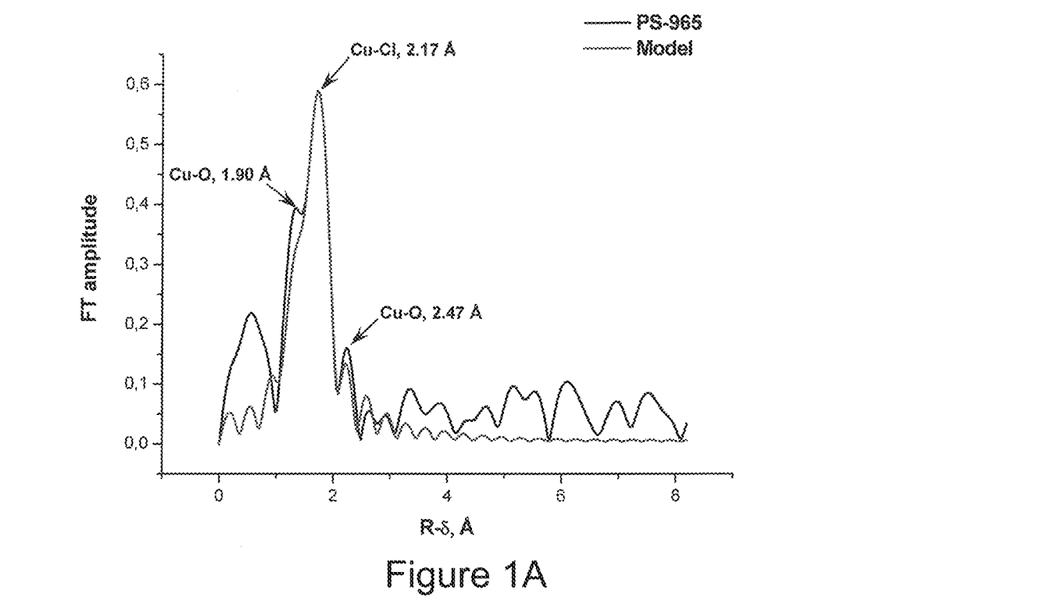
FIGS. 1A and 1B show the RDF curves, for before and after the process, for Catalyst I to demonstrate the existence of the mononuclear copper chloride complexes.
Figure 1B:
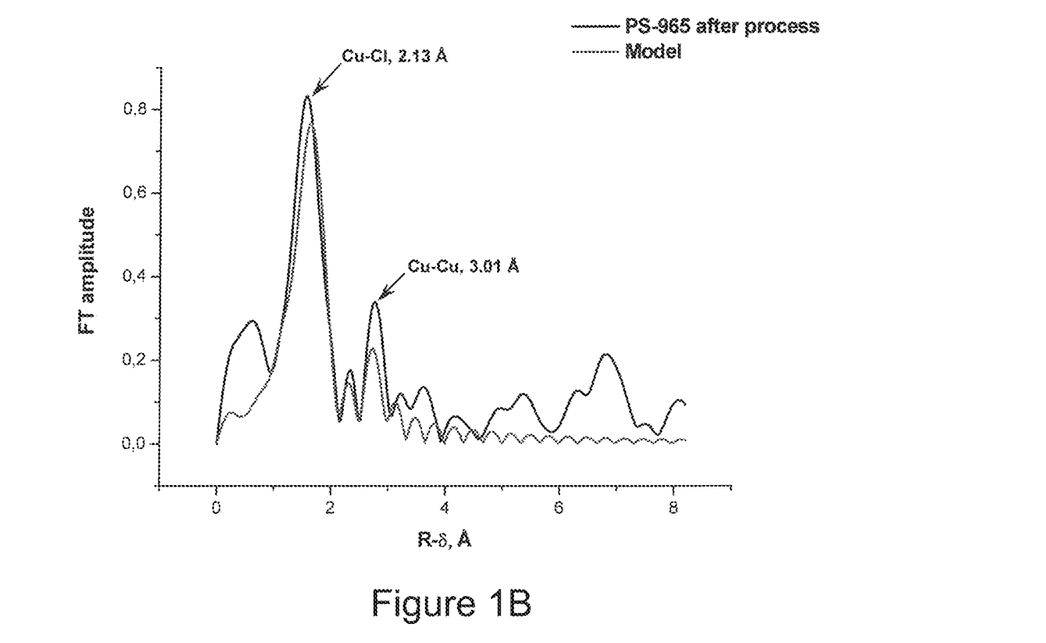

The macroporous ion exchangers have the active sites localized on the surface of the pores. This is in line with XPS results: at comparable average bulk Cu loading (12-14.5 wt %) the good catalyst has surface concentration of only ¼ of that of bad (i.e. active but non-selective) catalyst. This confirms that the active and selective Cu species are located inside the pores of anionite. EXAFS data provide further insight into the nature of Cu(I) species. As shown in FIGS. 1A and 1B, the radial distribution functions (RDF) of atoms around Cu show no presence of a Cu neighbor. The RDF contains an intense peak at R–δ=2.16 Å that corresponds to the Cu—Cl distance in the $[CuCl_2]^-$ complexes. We also observe the peak at R–δ=1.90 Å that can be classified as the Cu—O distance and the peak at R–δ=2.46 Å, corresponding to the Cu—O distance in the second coordination sphere of copper. The existence of these peaks are good indications that the active Cu species are mononuclear.

Figure 2A:
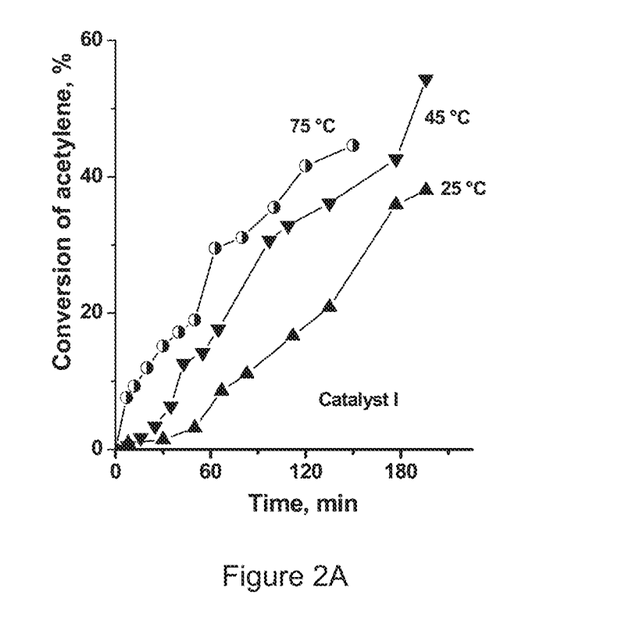
FIGS. 2A and 2B show the influence of temperature on the conversion of acetylene and vinylacetylene selectivity.
Figure 2B:
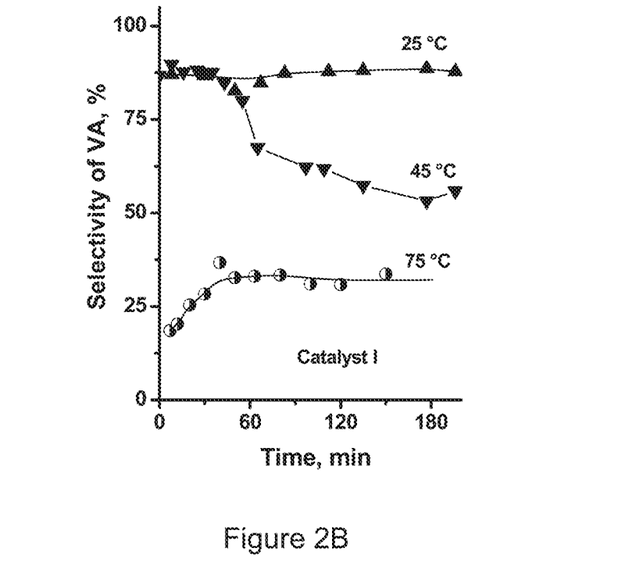

The results show a steady continuous activity over time tested, and for many of the heterogenous catalysts, a substantial selectivity. The reaction conditions include a pressure between 100 kPa (absolute) and 200 kPa (absolute), with a temperature between 25° C. and 100° C., with a preferred temperature between 55° C. and 75° C. It was found that conversion increases with temperature, but that the selectivity decreases with increasing temperatures. This can be seen in FIGS. 2A and 2B showing the conversions and selectivities.

Figure 3A:
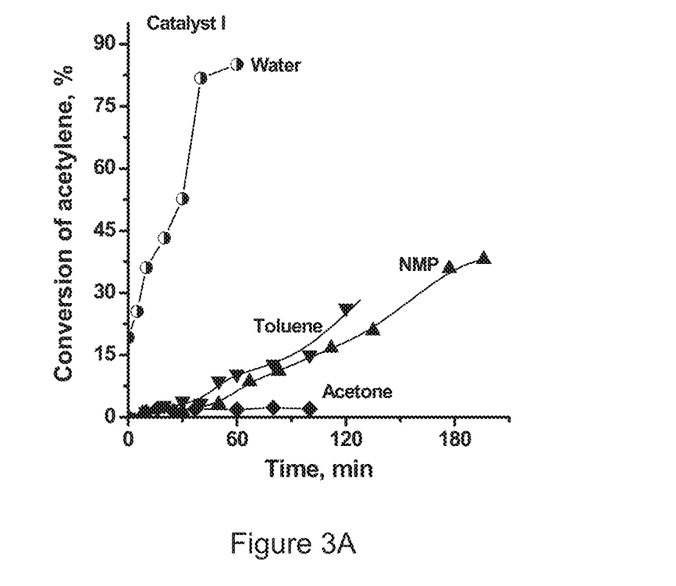
FIGS. 3A and 3B show the effect of choice of solvent on the conversion of acetylene and vinylacetylene selectivity.
Figure 3B:
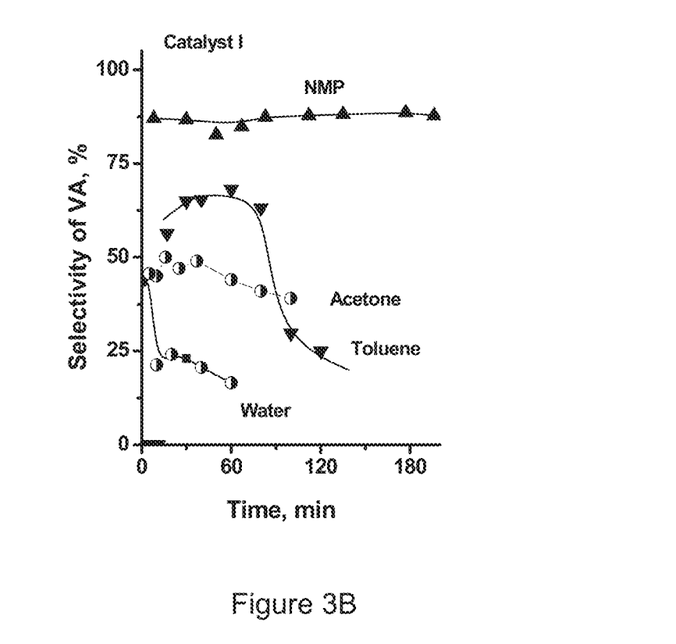

FIGS. 3A and 3B show the conversion of acetylene, and the selectivity of vinylacetylene for the catalyst in different solvents. The reaction conditions include flowing acetylene through the catalyst-solvent mixture at a temperature of 65° C. and atmospheric pressure.

Figure 4A:
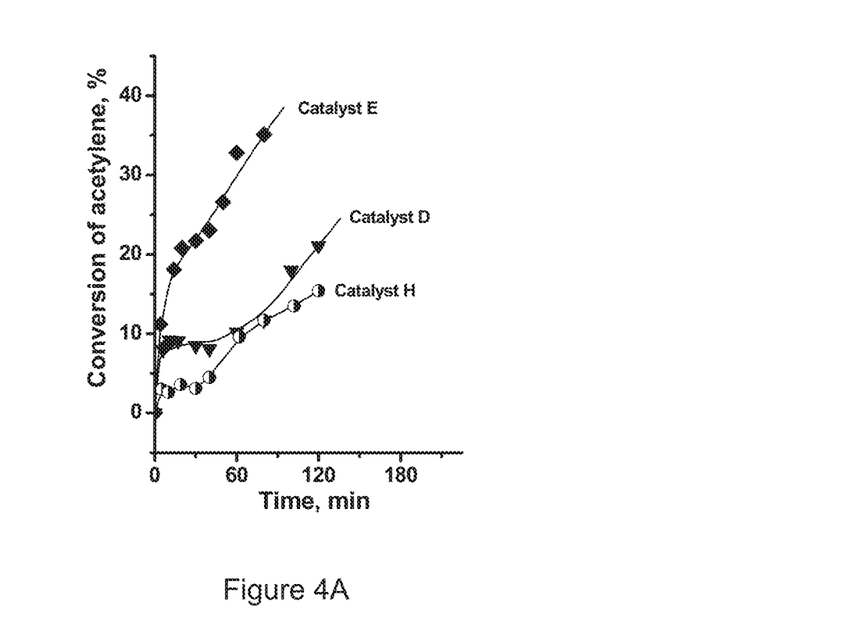
FIGS. 4A and 4B show the effect of the nature of the anionite on the conversion of acetylene and vinylacetylene selectivity.
Figure 4B:
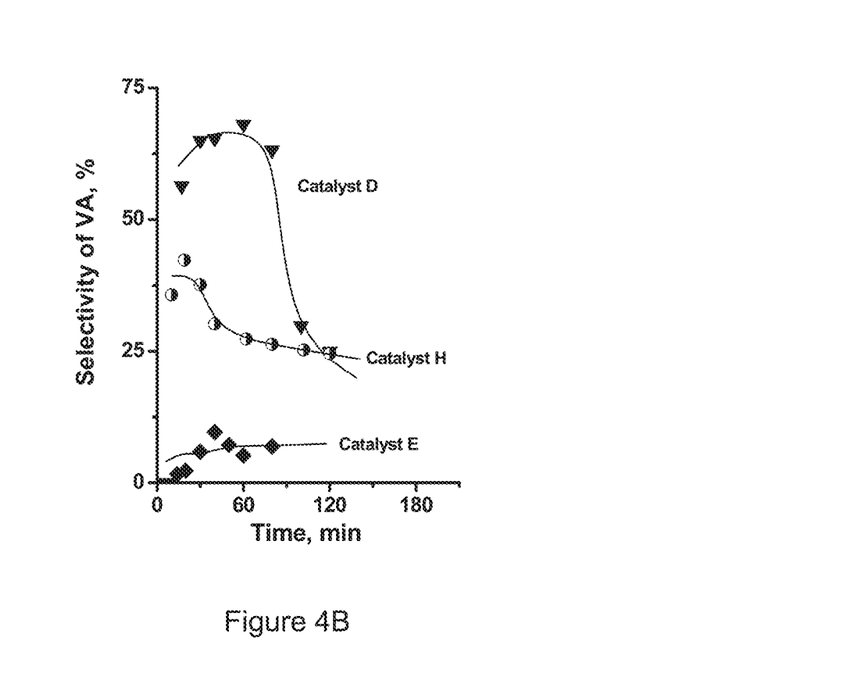

FIGS. 4A and 4B show the effect of the nature of the anionite on the activity and the selectivity of the catalysts. The nature includes the structure, such as the pore sizes and accessibility of the acetylene to the metal halide catalyst. The different catalysts can have different functional groups, a different basicity and capacity, and can have different particle sizes. The figures show the conversion and selectivity for three different catalysts having particles sizes and different functional groups.

Figure 5A:
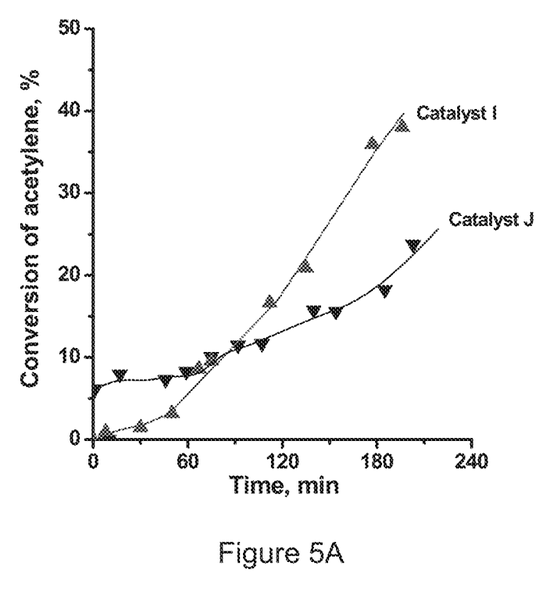
FIGS. 5A and 5B show the conversion of acetylene and vinylacetylene selectivity under batch operating conditions.
Figure 5B:
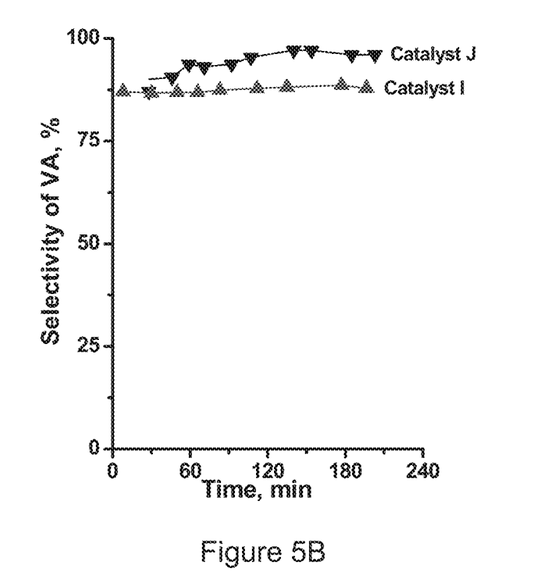

The process using the catalyst was also operated under batch conditions, with samples taken over time to check on the conversion of acetylene and the selectivity of the catalyst to produce vinylacetylene. The results, as seen in FIGS. 5A and 5B, showed consistently high selectivity, and a continuing conversion over time.

Numerous catalysts were formed and tested. Some of the catalysts presented include: Catalyst A is a polyethylene polyamine-epichloro-hydrin-NH$_3$ polycondensation type anionte, with secondary and tertiary aliphatic amino groups, and has weak basicity with a 2.6 mmol/ml capacity, and particle sizes in the range of 0.4 to 2 mm; Catalyst B is a polycondensation of melamine-formaldehyde condensate, with secondary and tertiary amino-groups linked with triazine fragment, and has weak basicity with a 1.7 mmol/ml capacity, and particles sizes in the range of 0.25 to 3 mm; Catalyst C is a polycondensation of polyethylene polyamine-phenol-formaldehyde condensate, with secondary and tertiary amino groups, and has weak basicity with a 2.6 mmol/ml capacity, and particle sizes in the range of 0.4 to 2 mm; Catalyst D is a macroporous styrene-divinylbenzene copolymer, with benzyltrimethyl ammonium groups, and has strong basicity with a 0.8 mmol/ml capacity, and particle sizes in the range of 0.3 to 1.25 mm; Catalyst E is a macroporous styrene-divinylbenzene copolymer, with tertiary and quaternary aminogroups, and has medium basicity with a 1.3 mmol/ml capacity, and particle sizes in the range of 0.52 to 0.62 mm; Catalyst F is a macroporous styrene-divinylbenzene copolymer, with secondary and tertiary N-groups, and has weak basicity with a 1.25 mmol/ml capacity, and particle sizes in the range of 0.55 to 0.75 mm; Catalyst G is a macroporous styrene-divinylbenzene copolymer, with secondary and tertiary N-groups, and has weak basicity with a 1.3 mmol/ml capacity, and particle sizes in the range of 0.49 to 0.69 mm; Catalyst H is a macroporous styrene-divinylbenzene copolymer, with benzyltrimethyl-ammonium groups, and has strong basicity with a 0.8 mmol/ml capacity, and particle sizes in the range of 0.3 to 1.25 mm; Catalyst I is a gel, styrene-divinylbenzene copolymer, with benzyltrimethyl ammonium groups, and has strong basicity with a 1.1 mmol/ml capacity, and particle sizes in the range of 0.3 to 1.25 mm; Catalyst J is a gel, styrene-divinylbenzene copolymer, with benzyltrimethyl ammonium groups, and has strong basicity with a 1.1 mmol/ml capacity, and particle sizes in the range of 0.3 to 1.25 mm; and Catalyst K is a crosslinked acrylic gel polymer, and has medium basicity with a 1.6 mmol/ml capacity, and particles sizes in the range of 0.5 to 0.75 mm.

The results for polycondensation type anionites (Catalysts A-H) and gel-type anionites (Catalysts I-K) are shown in the following table. The gel type anionite catalyst showed high selectivities and conversion, whereas the polycondensation type of catalyst varied to a greater extent in selectivities, but demonstrated good conversions.

TABLE

Influence of the nature of support on acetylene conversion and selectivity to vinylacetylene (VA) at 65° C. (amount of catalyst 1.3 g).

| Run | Catalyst | time (min) | conversion of C$_2$H$_2$ (%) | selectivity of VA (%) |
|---|---|---|---|---|
| 1 | A | 30 | 4.8 | 23.2 |
|  |  | 60 | 5.6 | 29.6 |
|  |  | 90 | 6.3 | 31.9 |
| 2 | B | 30 | 6.2 | 90.1 |
|  |  | 60 | 9.2 | 83.2 |
|  |  | 90 | 11.3 | 56.6 |
| 3 | C | 30 | 2.7 | 61.4 |
|  |  | 60 | 4.5 | 56.2 |
|  |  | 90 | 9.1 | 56.8 |
| 4 | D | 30 | 8.2 | 64.9 |
|  |  | 60 | 10.6 | 65.8 |
|  |  | 90 | 14.5 | 44.3 |
| 5 | E | 30 | 21.7 | 5.3 |
|  |  | 60 | 32.9 | 6.2 |
|  |  | 90 | 37.9 | 6.5 |
| 6 | F | 30 | 3.6 | 54.5 |
|  |  | 60 | 5.9 | 53.1 |
|  |  | 90 | 6.7 | 52.8 |
| 7 | G | 30 | 1.5 | 77.8 |
|  |  | 60 | 1.8 | 63.9 |
|  |  | 90 | 1.9 | 59.5 |
| 8 | H | 30 | 3.0 | 37.6 |
|  |  | 60 | 9.6 | 27.3 |
|  |  | 90 | 12.3 | 25.2 |
| 9 | I | 30 | 2.3 | 87.8 |
|  |  | 60 | 6.2 | 87.8 |
|  |  | 90 | 12.3 | 87.8 |
| 10 | J | 30 | 7.3 | 90.3 |
|  |  | 60 | 8.1 | 93.4 |
|  |  | 90 | 11.3 | 94.0 |
| 11 | K | 30 | 1.2 | 96.2 |
|  |  | 60 | 1.4 | 97.0 |
|  |  | 90 | 1.4 | 92.7 |

While the invention has been described with what are presently considered the preferred embodiments, it is to be understood that the invention is not limited to the disclosed embodiments, but it is intended to cover various modifications and equivalent arrangements included within the scope of the appended claims.

SPECIFIC EMBODIMENTS

While the following is described in conjunction with specific embodiments, it will be understood that this description is intended to illustrate and not limit the scope of the preceding description and the appended claims.

A first embodiment of the invention is a catalyst for the dimerization of acetylene under dimerization conditions comprising an ion exchange resin with an exchangeable anion (hydroxide or halide ion) to form an exchanged resin including the halide; and the exchanged resin is compounded with a metal halide. An embodiment of the invention is one, any or all of prior embodiments in this paragraph up through the first embodiment in this paragraph wherein the halide compound is selected from the group consisting of amines, phosphines, and mixtures thereof. An embodiment of the invention is one, any or all of prior embodiments in this paragraph up through the first embodiment in this paragraph wherein the amine has the form of NR1R2R3, and the phosphine has the form PR1R2R3. An embodiment of the invention is one, any or all of prior embodiments in this paragraph up through the first embodiment in this paragraph wherein the R1, R2, R3 groups are selected from the group consisting of hydrogen, alkyl groups, aryl groups, and mixtures thereof. An embodiment of the invention is one, any or all of prior embodiments in this paragraph up through the first embodiment in this paragraph wherein the R1, R2, R3 groups are the same alkyl group or the same aryl group. An embodiment of the invention is one, any or all of prior embodiments in this paragraph up through the first embodiment in this paragraph wherein the metal halide is selected from the group consisting of cuprous chloride (CuCl), silver chloride (AgCl), ferrous chloride ($FeCl_2$), ferric chloride ($FeCl_3$), nickel chloride ($NiCl_2$), chlorides of gold (AuCl and $AuCl_3$), or mixtures thereof. An embodiment of the invention is one, any or all of prior embodiments in this paragraph up through the first embodiment in this paragraph wherein the metal halide is cuprous chloride. An embodiment of the invention is one, any or all of prior embodiments in this paragraph up through the first embodiment in this paragraph wherein the ion exchange resin comprises a polymer backbone selected from the group consisting of styrene, divinylbenzene, styrene-divinylbenzene co-polymer, polyethylene, polyamine-epichlorohyrdin-$NH_3$ condensate, melamine-formaldehyde condensate, polyamine-phenol-formaldehyde condensate, melamine-formaldehyde condensate, polyamine-phenol-formaldehyde condensate, cellulose and mixtures thereof.

A second embodiment of the invention is a catalyst comprising a polymer backbone with a plurality of functional groups, wherein the functional groups are selected phosphonium chlorides and amine chlorides; and the functional groups are ion exchanged with metal chlorides. An embodiment of the invention is one, any or all of prior embodiments in this paragraph up through the second embodiment in this paragraph wherein the polymer backbone is selected from the group consisting of styrene, divinylbenzene, styrene-divinylbenzene co-polymer, polyethylene, polyamine-epichlorohyrdin-$NH_3$ condensate, melamine-formaldehyde condensate, polyamine-phenol-formaldehyde condensate, melamine-formaldehyde condensate, polyamine-phenol-formaldehyde condensate, cellulose and mixtures thereof. An embodiment of the invention is one, any or all of prior embodiments in this paragraph up through the second embodiment in this paragraph wherein the amine in the amine chloride has the form of NR1R2R3, and the phosphine in the phosphonium chloride has the form PR1R2R3. An embodiment of the invention is one, any or all of prior embodiments in this paragraph up through the second embodiment in this paragraph wherein the R1, R2, R3 groups are selected from the group consisting of hydrogen, alkyl groups having from 1 to 4 carbon atoms, aryl groups and mixtures thereof. An embodiment of the invention is one, any or all of prior embodiments in this paragraph up through the second embodiment in this paragraph wherein R1, R2, R3 are selected from the group consisting of H, $CH_3$, $C_2H_5$, or mixtures thereof. An embodiment of the invention is one, any or all of prior embodiments in this paragraph up through the second embodiment in this paragraph wherein the metal chloride is selected from the group consisting of cuprous chloride (CuCl), silver chloride (AgCl), ferrous chloride ($FeCl_2$), ferric chloride ($FeCl_3$), nickel chloride ($NiCl_2$), chlorides of gold (AuCl and $AuCl_3$), or mixtures thereof. An embodiment of the invention is one, any or all of prior embodiments in this paragraph up through the second embodiment in this paragraph wherein the metal chloride is cuprous chloride. An embodiment of the invention is one, any or all of prior embodiments in this paragraph up through the second embodiment in this paragraph wherein the polymer backbone is selected from the group consisting of styrene, divinylbenzene, styrene-divinylbenzene co-polymer, polyethylene, polyamine-epichlorohyrdin-$NH_3$ condensate, melamine-formaldehyde condensate, polyamine-phenol-formaldehyde condensate, melamine-formaldehyde condensate, polyamine-phenol-formaldehyde condensate, cellulose and mixtures thereof.

A third embodiment of the invention is a process for the production of 1,3 butadiene, comprising dimerizing a first process stream comprising acetylene, under dimerization conditions, in the presence of a catalyst comprising a polymer backbone with a plurality of functional groups affixed to the polymer backbone wherein the functional groups have a positive charge and a charge balancing anion, and at least one of the anions is ion exchanged with a metal halide, that is converted to anion form, to generate a polymer with metal halide groups ionically bonded to the functional groups, to generate a second process stream comprising vinylacetylene, wherein the functional groups are selected from the group consisting of amines, phosphines and mixtures thereof; hydrogenating the vinylacetylene in the second process stream to generate a third process stream comprising 1,3 butadiene. An embodiment of the invention is one, any or all of prior embodiments in this paragraph up through the third embodiment in this paragraph wherein the metal is selected from the group consisting of copper, iron, silver and mixtures thereof. An embodiment of the invention is one, any or all of prior embodiments in this paragraph up through the third embodiment in this paragraph wherein the hydrogenating of vinyl acetylene is performed in a reactor with a selective hydrogenation catalyst. An embodiment of the invention is one, any or all of prior embodiments in this paragraph up through the third embodiment in this paragraph wherein the polymer backbone is selected from the group consisting of styrene, divinylbenzene, styrene-divinylbenzene co-polymer, polyethylene, polyamine-epichlorohyrdin-$NH_3$ condensate, melamine-formaldehyde condensate, polyamine-phenol-formaldehyde condensate, melamine-formaldehyde condensate, polyamine-phenol-formaldehyde condensate, and mixtures thereof.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for the production of 1,3 butadiene, comprising:
    dimerizing a first process stream comprising acetylene, under dimerization conditions, in the presence of a catalyst comprising a polymer backbone with a plurality of functional groups affixed to the polymer backbone wherein the functional groups have a positive charge and a charge balancing anion, and at least one of the anions is ion exchanged with a metal halide, that is converted to anion form, to generate a polymer with metal halide groups ionically bonded to the functional groups, to generate a second process stream comprising vinylacetylene, wherein the functional groups are selected from the group consisting of amines, phosphines and mixtures thereof;

hydrogenating the vinylacetylene in the second process stream to generate a third process stream comprising 1,3 butadiene.

2. The process of claim 1 wherein the metal is selected from the group consisting of copper, iron, silver and mixtures thereof.

3. The process of claim 1 wherein the hydrogenating of vinyl acetylene is performed in a reactor with a selective hydrogenation catalyst.

4. The process of claim 1 wherein the polymer backbone is selected from the group consisting of styrene, divinylbenzene, styrene-divinylbenzene co-polymer, polyethylene, polyamine-epichlorohyrdin-NH3 condensate, melamine-formaldehyde condensate, polyamine-phenol-formaldehyde condensate, and mixtures thereof.

* * * * *